United States Patent [19]

Cheng

[11] Patent Number: 4,886,584
[45] Date of Patent: Dec. 12, 1989

[54] POTENTIAL MEASURING METHOD AND APPARATUS HAVING SIGNAL AMPLIFYING MULTIPLE MEMBRANE ELECTRODE

[75] Inventor: Kuang L. Cheng, Kansas City, Mo.

[73] Assignee: Solar Scientific, Inc., Kansas City, Mo.

[21] Appl. No.: 212,051

[22] Filed: Jun. 27, 1988

[51] Int. Cl.⁴ ............................................. G01N 27/30
[52] U.S. Cl. ..................... 204/1 T; 204/406; 204/412
[58] Field of Search ............... 204/406, 412, 1 T, 416, 204/418, 419, 420

[56] References Cited

U.S. PATENT DOCUMENTS

| | | | |
|---|---|---|---|
| 870,674 | 11/1907 | Guess et al. | 204/400 |
| 3,248,309 | 4/1966 | Robinson | 204/1 T |
| 3,399,667 | 9/1968 | Nishimoto et al. | 128/631 |
| 3,556,950 | 1/1971 | Dahms | 204/1 R |
| 3,598,712 | 8/1971 | Petersen | 204/420 |
| 3,787,307 | 1/1974 | Schwab et al. | 204/420 |
| 3,806,440 | 4/1974 | Gray et al. | 204/420 |
| 4,008,141 | 2/1977 | Kotani et al. | 204/420 |
| 4,133,732 | 1/1979 | Boeke | 204/412 |
| 4,155,814 | 5/1979 | Tejfalussy et al. | 204/1 T |
| 4,404,065 | 9/1983 | Matson | 204/1 T |
| 4,519,890 | 5/1985 | Uematsu et al. | 204/409 |
| 4,595,487 | 6/1986 | Nunlist | 204/433 |
| 4,647,362 | 3/1987 | Watanabe | 204/411 |
| 4,664,772 | 5/1987 | Zaccari et al. | 204/400 |
| 4,686,011 | 8/1987 | Jäckle | 204/1 T |

FOREIGN PATENT DOCUMENTS 2709173 9/1978 Fed. Rep. of Germany .

OTHER PUBLICATIONS

Kuang L. Cheng et al., "Evidence of Adsorption of Hydrogen and Hydroxide Ions by pH-Sensitive Glass and Chemical Potential Amplification", J. Chem. Soc. Communications (1988).

*Primary Examiner*—G. L. Kaplan
*Attorney, Agent, or Firm*—Hovey, Williams, Timmons & Collins

[57] ABSTRACT

Ionic concentration in a solution is measured using a multiple membrane electrode potential amplification device. The apparatus includes a plurality of potential sensing membranes and reference elements. Preferably at least four of the membranes and associated elements are all connected in electrical series relationship and joined to the terminals of a potential measuring meter such that the potential read out by the meter is equal to the sum of all of the individual membrane potentials. Amplification of the electrode potential is obtained by virtue of the fact that the individual membranes function as capacitors in a series circuit with the potential measuring meter. The membranes may be placed in separate sample containing vessels, or a unitary test device may be provided having individual compartments for the test solution.

20 Claims, 3 Drawing Sheets

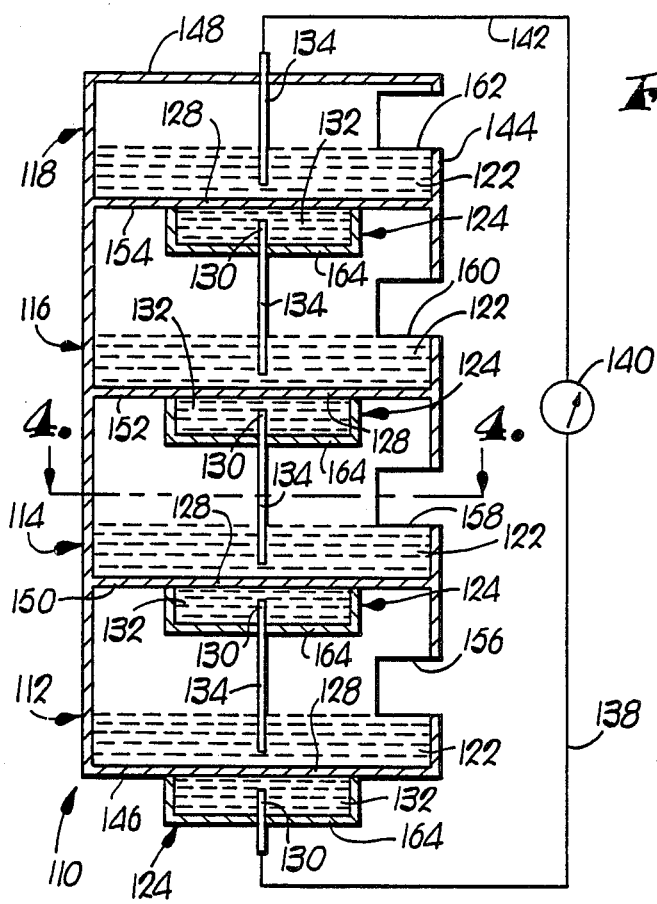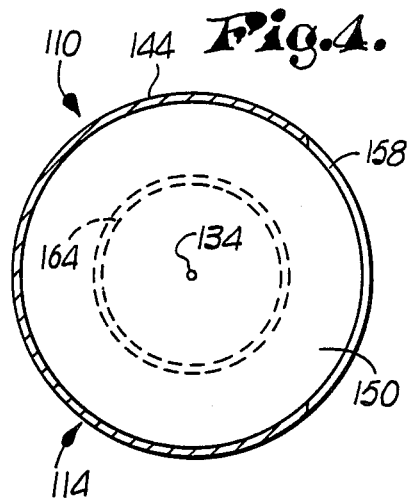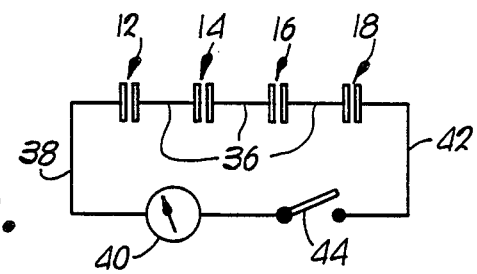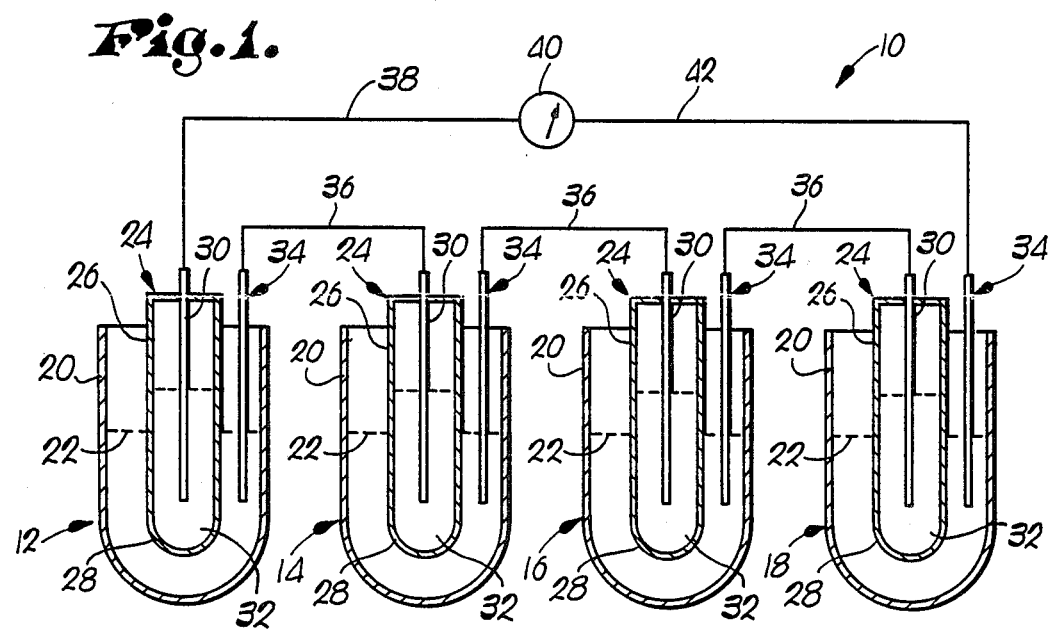

POTENTIAL MEASURING METHOD AND APPARATUS HAVING SIGNAL AMPLIFYING MULTIPLE MEMBRANE ELECTRODE

BACKGROUND OF THE INVENTION

1. Field of the Invention

This invention relates to potentiometric measurement of ion activity or concentration in a solution. Specifically, it relates to a multiple membrane electrode device which amplifies the potential directed to measuring apparatus therefor by virtue of the fact that the potential sensing electrodes and reference elements associated with each membrane are connected in electrical series relationship to the apparatus.

2. Summary of Prior pH Glass Electrode Practices and Theories

The potentiometric measurement of the cationic and anionic activity in a solution has long been conducted using ion selective electrodes and a reference electrode which are both immersed in the solution to be tested and electrically connected to a potential measuring device such a pH meter or potentiometer.

In the case of pH measurements, the sensing or indicating electrode usually is made up of a non-conducting glass tube called the body which has a bulb sealed thereto made up of special conductive glass generally called the pH sensing membrane. The glass body is filled with a buffered electrolyte whose pH value and ionic concentration are fixed. An internal reference member is immersed in the buffered electrolyte solution. Typically, the reference member may be Ag/AgCl. This configuration assures that constant potentials are developed on the inner surface of the glass membrane and on the internal reference member. Thus, when the electrode is immersed in a solution of pH 7, the sum of these fixed voltages approximately balances the voltage developed on the outer surface of the glass membrane and a separate reference element. Under these conditions, the total potential output of the system is very nearly 0 mV.

The reference element serves to complete the electrical measuring circuit. A simple electrically conductive wire immersed in the sample solution will satisfy this purpose. However, in actual practice, the use of a conductive wire is susceptible to voltage changes, dependent on the time and solution and the sample composition. In order to avoid this problem, it is the general practice to use a reference element, e.g., calomel or Ag/AgCl immersed in an electrolyte filling solution of fixed ionic concentration contained in the probe body. This produces the required constant voltage, no matter what the sample composition. The electrical circuit is completed by allowing a small flow of the electrolyte to pass through a porous junction in the probe tip.

A combination pH measuring electrode containing both a pH sensing electrode and a reference element combined in a single probe body have also long been available. The annular space surrounding the inner tube contains the reference element and electrolyte. Solution contact is made through a porous junction in the outer wall. The combination electrode has the advantage of convenience in field use and the ability to take measurements in small sample vessels where an electrode pair would not fit.

Since the early 1900's, when the first observations were made of the potentiometric relationship of a glass membrane with a pH solution, various attempts have been made to explain the glass membrane potential. Although the pH glass electrode is one of the most widely used analytical tools, it is believed to be one of the least understood. Prior investigators have attempted to explain that the potential of a thin glass film is attributed to the selective permeability of mobility of the H+ ion across the glass-aqueous solution interface. The concept of an actual penetration through the glass membrane by hydrogen ions was first disproved in the 1940's and reaffirmed in the 1960's. Notwithstanding this clear evidence to the contrary, some investigators still incorrectly cling to the theory that the glass membrane is permeable to the H+ ion.

The now disproved adsorption-potential theory postulated an adsorbed layer of hydrogen ions on the glass surface causing a potential drop at the glass-solution interface, corresponding to the difference in chemical potential between the free and adsorbed ions. It was suggested that the gel layer of the glass membrane acted as an ion exchanger producing a phase boundary potential at which the H+ ion exchanged with the Na+ ion. Experimental results do not support this ambiguous proposal. If such an exchange did occur, there would be no net change in interfacial charges. Furthermore, the sodium ion in the gel layer of the membrane would eventually be depleted after long usage resulting in a failure of the glass electrode. However, it is well established that pH glass electrodes have a long useful life. It is also known that a quartz glass membrane containing no sodium is useful as a pH glass electrode.

It appears that prior investigators devoted an inordinate amount of time to interpreting the phenomena of glass electrodes for pH measurement purposes in thermodynamic terms. Nernst equations, which in simplified form may be expressed as $$E = E_o - \frac{2.303}{F} \times RT(\text{pH})$$

where E equals the measured voltage; $E_o$ is the total of all constant voltages in the measuring system; R is the Gas Law constant; T is the temperature in °K; and F is Faraday's constant. However, more recent investigators have pointed out that in using this mathematical relationship, electrochemists have in effect tried to do the impractical, i.e., treat highly thermodynamically irreversible electrode reactions by a series of approximations and perceived misconceptions on the basis of reversible thermodynamics. Quantitative and instrumental analyses have inaccurately treated the glass electrode as a battery obeying the principles of reversible thermodynamics and the Nernst equations.

Similarly, ionic activity other than H+ and OH− in solutions has long been analyzed using an ion selective sensing electrode and a reference element immersed in the solution. For example, in order to determine the cations and anions present in a solution involving metal ions, the sensing electrode is generally of the same cation as that to be sensed. If the ionic activity of copper in a copper solution is to be measured, then a copper sensing electrode is utilized with an appropriate reference element which may be a simple electrically conductive wire as previously indicated.

3. Summary of New Theory

A battery is a device containing no insulator and producing an electric current through chemical redox reactions that occur in cells that are placed in series.

Each cell contains an anode and a cathode that are immersed in an electrolyte medium. Connecting the anode and the cathode to the external circuit causes an electric current flow until chemical reactions cease. Mostly it is reversible, following the principles of equilibrium thermodynamics, i.e., the Nernst equation. On the other hand, a capacitor is a device for storing electric charges through two conducting plates between which there is a dielectric in which no reversible redox reaction takes place. By connecting two charging plates, no significant current flows. For a capacitor, C =q/V, where C is the capacitance, q is the charge and V is the potential difference.

An ion sensing electrode may be generally represented in a cell as follows wherein the cation in a solution is represented as $M^+$:

| Ref. Electrode | $M^+$ known | Glass membrane | $M^+$ (unknown) | Ref. Electrode |

$$E_{electrode} = \text{constant} + 0.05916 \log \frac{A_{M^+} \text{ (unknown)}}{A_{M^+} \text{ (known)}}$$

It has been recognized for a long time that there are no redox reactions involved in the potential development of glass electrode. Based on the definitions of a battery and a capacitor, it is not accurate to say that the electrode component of a pH measuring system is comparable to a battery where voltage changes with pH. Instead, it is believed that a potential sensing electrode in conjunction with a reference element is comparable to a capacitor rather than to a battery.

4. Description of the Prior Art

Measurement of the ionic potential test solutions with a plurality of test units has previously been suggested, but the electrodes have not been placed in electrical series relationship to function as capacitors which amplify the signal such that the total potential is equal to the sum of each individual membrane electrode potential.

U.S. Pat. No. 4,155,814 issued to Tejfalussy, et al. on May 22, 1979 describes an electrode system consisting of a number of working electrodes as well as a series of counterelectrodes and reference electrodes in series. In one embodiment, a single extended electrode membrane is provided with a number of individual reference electrodes in electrical parallel relationship. This device permits measurements simultaneously at a number of points equal to the number of reference electrodes. However, the result is simply to permit measurement of pH over a relatively wide area and there is no amplification of the signal.

In Dahms U.S. Pat. No. 3,556,950 issued Jan. 19, 1971, a plurality of electrodes each sensitive to a different dissolved gas or ion and a single reference electrode are connected in series so that a sequential measurement may be made of the different gas or ion to be analyzed. In Robinson U.S. Pat. No. 3,248,309 issued Jan. 26, 1966 describes an automatic titrator wherein continuous analysis may be carried out on very small quantities of the solution to be tested. In U.S. Pat. No. 870,674 of Nov. 12, 1907 in the name of Guess, et al., samples to be tested electrochemically may be analyzed in a predetermined sequential series.

Other patents disclosing multiple electrodes include Schwab, U.S. Pat. No. 3,787,307 of Jan. 22, 1974; Boeke, U.S. Pat. No. 4,133,732 of Jan. 9, 1979; Mattson, U.S. Pat. No. 4,404,065 of Sept. 13, 1983; Vematsu, U.S. Pat. No. 4,519,890 of May 28, 1985; Watanabe, U.S. Pat. No. 4,647,362 of Mar. 3, 1987; and Jackle, U.S. Pat. No. 4,686,011 of Aug. 11, 1987.

SUMMARY OF THE INVENTION

An electrode capacitor may be considered as a membrane material made from either a dielectric or a semiconductor which can adsorb cations and anions on its active sites. The membrane potential is believed to derive from the two interfaces that hold charges on the surface through double layer adsorptions. The sensing electrode/reference element potential follows the capacitance law.

$$E = \frac{q}{C} = \frac{q\,d}{k\,A\,\epsilon}$$

where k is the dielectric constant of the glass membrane, $\epsilon$ is the permittivity, A is the membrane area, d is the membrane thickness, q is the charge, and C is the capacitance of the membrane. When $\epsilon$, K, A, d, and C are constant for the same electrode membrane, E is then proportional to q ($q_{30}$ is the positive charge, $q_{31}$ is the negative charge). Then, $$E = K(\Sigma q_{30} - \Sigma q_{31})$$

where K is a new constant. If only cations ($H^+$) are adsorbed on the membrane surface, $\Sigma q_- = 0$, resulting in the potential increasing with increasing positive charges; if only anions are adsorbed ($OH^-$), $\Sigma q_{30} = O$, resulting in the potential decreasing with increasing negative charges; and if both cations and anions are adsorbed simultaneously, the result is the sum of positive and negative charges (net charges).

From the last equation above, besides the charges, the membrane potential is affected by the surface area (A) and the thickness (d). The capacitance of the electrode membrane has been measured as a function of pI. The membrane electrodes thus clearly function as capacitors.

Recognizing that the membrane electrodes are capacitors, it has now been discovered that if the sensing electrodes and reference elements are connected in electrically series relationship and associated with separate quantities of the solution to be analyzed for the ionic value thereof, and that if the endmost sensing electrode and opposite endmost reference element are connected to opposite terminals of a potential measuring meter, the resulting output of the meter in volts is a function of the additive voltage values of the electrodes. This amplification of the signal significantly increases the sensitivity of the potential measurement and thus enhances accuracy of the reading.

Measurement of the ionic activity may be accomplished by using a plurality of series connected sensing electrodes and reference elements each immersed in a separate quantity of the solution to be measured, or a stacked arrangement of electrodes in a single body may be employed with the solution introduced into individual compartments in the body.

BRIEF DESCRIPTION OF THE DRAWINGS

FIG. 1 is a schematic vertical crosssectional representation of amplified signal potential measuring apparatus made in accordance with a second preferred embodiment of the invention;

FIG. 2 is a schematic electrical representation of the invention illustrating the manner in which the sensing electrodes and reference elements function as capacitors connected in electrical series relationship with potential measuring apparatus and a control switch;

FIG. 3 is a schematic vertical crosssectional representation of amplified signal potential measuring apparatus made in accordance with one preferred embodiment of the invention;

FIG. 4 is a horizontal cross-sectional view on the line 4—4 of FIG. 3;

DETAILED DESCRIPTION OF THE INVENTION

Figure 5:
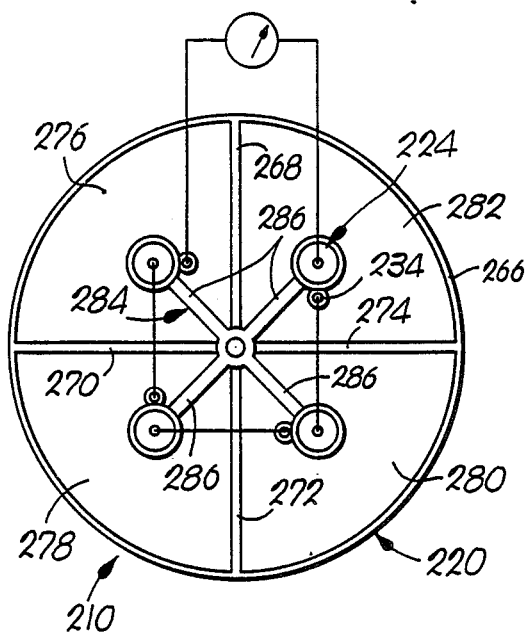
FIG. 5 is a plan view of amplified signal potential measuring apparatus made in accordance with a third preferred embodiment of the invention and illustrating the electrical circuitry and associated meter in schematic fashion.

Referring initially to FIGS. 1 and 2, an amplified potential signal measuring device is schematically illustrated and broadly designated by the numeral 10. In this device, four electrically series connected units 12, 14, 16 and 18 respectively are illustrated although it is to be understood that any number of units may be provided depending upon the signal amplification desired. At least two units are necessary in all instances; however, more than four ionic activity measuring devices may be employed for greater signal amplification.

Each of the units 12–18 has an open topped vessel 20 adapted to receive a quantity of solution 22 that is to be tested for the ionic activity value thereof. It is to be understood in this respect that the composition of solution 22 introduced into each of the vessels 20 should be identical in order to obtain reliable ionic analysis results.

Immersed in the solution 22 within each vessel 20 is a potential sensing electrode broadly designated 24. Each sensing electrode 24 has a glass body 26 if pH measurements are to be taken, or a suitable ion selective electrode if other ionic solutions are to be tested. The electrodes 24 each have a membrane portion 28 at the lower end thereof. An internal reference member 30 is carried within each of the bodies 26 in disposition such that it contacts the buffered electrolyte 32 within each electrode 24. It is to be understood in this respect that member 30 is shown diagrammatically only and that the actual configuration thereof is a matter of choice and that the member may be a conventional Ag/AgCl component in the case of pH measurements, or a suitable ion selective component in the instance of metallic ion activity measurements.

Reference elements 34 are provided in each of the units 12–18 inclusive in disposition such that they are in electrically contacting and conductive relationship with the test solution received in corresponding vessels 20. The elements 34 are shown schematically in FIG. 1 but it is to be understood that such elements normally would not consist merely of electrically conductive wires, although such arrangement would be fully operable for purposes of the present invention, but instead may be conventional reference elements as previously described. For example, where pH measurements are to be taken of relative H+ and OH− activity, the reference element generally will have an internal reference member, usually calomel or Ag/AgCl immersed in electrolyte filling solution of fixed ionic concentration.

The reference elements 34 of units 12, 14 and 16 respectively may be connected by wires 36 to the internal reference member of units 14, 16 and 18 respectively. Wire 38 is adapted to join the internal reference member 30 of unit 12 to a terminal of the potential measuring meter diagrammatically illustrated and designated by the numeral 40 while wire 42 couples the other terminal of potential measuring meter 40 to the reference element 34 of unit 18.

The electrical schematic for device 10 is illustrated in FIG. 2. It can be seen that each of the units 12, 14, 16 and 18 effectively function as capacitors which are in electrical series relationship with the meter 40. For convenience of operation, a control switch 44 may be provided in the electrical conductive path 42 between meter 40 and unit 18.

In operation of device 10, the solution 22 to be measured is introduced into vessels 20 of each of the units 12–18 and electrodes 24 and elements 34 are immersed below the level of the solutions to be tested such that the membrane portions 28 of each of the electrodes 24 contact the test solution and elements 34 are similarly immersed in the liquid. Meter 40 is then operated in a conventional manner taking into account variations in temperature of the test solution and any compensation that must be provided for voltage levels.

Because the units 12–18 inclusive serve as capacitors in a series electrical circuit, the total potential equals the sum of the individual membrane electrode potentials in accordance with the following mathematical relationship:

$$\frac{1}{C} = \frac{1}{C_1} + \frac{1}{C_2} + \frac{1}{C_3} + \frac{1}{C_4} \cdots$$

where C=capacitance. Thus, the voltage relationship may also be expressed as:

$$E_{Total} = E_1 + E_2 + E_3 + E_4 \ldots$$

In order to verify the validity of the capacitance function of multiple sensing electrodes and reference elements in association with corresponding membranes therefor, tests were conducted using a tubular pH glass electrode for quantitative determination of the charge density effect on potential. A cylindrical and pH sensitive glass electrode of 1.0 cm×1.5 cm was specially prepared and used as a substitute for a pH bulb electrode. The whole section of the tube was sensitive to pH, when sealed, and the tube contained a pH 7 phosphate buffer solution and a Ag/AgCl reference electrode. The outer surface of the tubular electrode exposed to the test solution was controlled by the depth of immersion, i.e., the amount of charge on the same whole membrane surface area varied as a function of immersion depth. Different amounts of H+ or OH− were adsorbed on the surface as a result of varying depth of immersion of the tubular electrode into the same solutions. In acid solutions, the potentials increase with increasing depth of immersion. Similarly, in basic solutions the potentials decrease with increasing depth of immersion. At approximately pH 5.5 (isoelectric point of the glass membrane), the potential remains the same regardless of the depth of immersion (the point of zero change, pzc). In acid media, the increased positive potentials are the result of the increased adsorption of H+ ions on the electrode surface. In basic media, the increased negative potentials are the result of the increased adsorption of OH− ions on the electrode surface (or possibly neutralizing the surface proton). These studies demonstrated that the pH glass electrode is a pH electrode in an acid medium, but it is a pOH sensor in a basic medium. It therefore is a pOH electrode in basic solutions. This has been evidenced by the negative charges of the glass membrane in basic solutions. This is evidenced of the fundamental differences between my capacitor theory and the past theories which have not adequately considered the role of OH− ions in the development of voltage potential. Thus, the concentration of OH− has not heretofore been properly included in cell diagrams and the Nernst equation.

Figure 8:
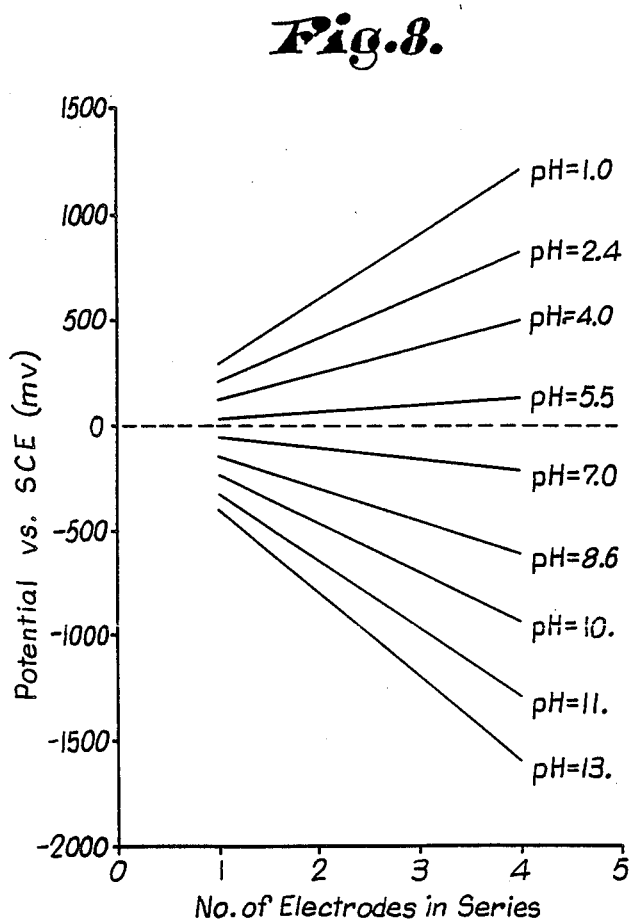
FIG. 8 is a graphical representation of the signal amplification obtained by use of devices as illustrated in the preceding figures for measurement of pH using glass sensing electrodes and associated reference elements, as compared with a single sensing electrode and reference element for pH measurement.

Additional tests utilizing a device as illustrated in FIG. 1 were conducted to verify that glass pH electrodes when connected in electrical series relationship to a pH meter amplify the signal. The results of these tests are recorded in the chart of FIG. 8 wherein it can be seen that the electrical potential versus a single copper electrode produced an emf after amplification that exceeded 1 volt for both pH 1.0 and 13.0. In the chart, the designation "SCE" means saturated calomel electrode.

Figure 9:
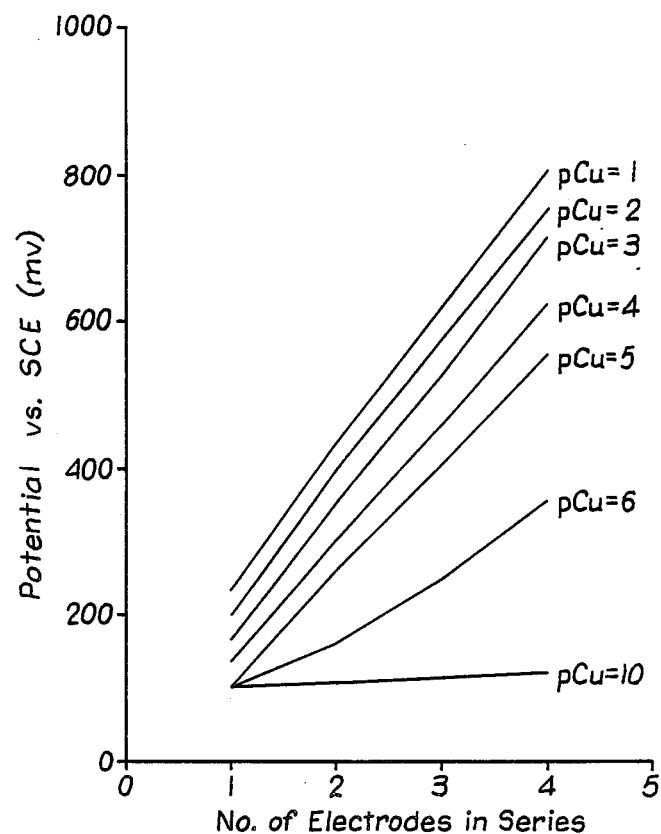
FIG. 9 is a graphical representation of the signal amplification which is obtained when the ionic activity in a copper solution is measured using a copper sensing electrode and a reference element, as compared with a single copper sensing electrode and reference element.

The results of tests demonstrating amplification of the potential signal obtained during measurement of the ionic activity of a copper solution, is illustrated in FIG. 9 utilizing copper sensing electrodes and associated multiple membranes.

In the second preferred embodiment of the invention illustrated in FIGS. 3 and 4, the single amplified potential signal electrode device is designated by the numeral 110. The cylindrical device 110 is provided having a series of units 112, 114, 116, and 118 respectively. The device 110 has a cylindrical side wall 144 along with a bottom wall 146 and a top wall 148. Vertically spaced, intermediate cross walls 150, 152 and 154 are provided in spanning relationship to cylindrical wall 144 between bottom wall 146 and top wall 148. Preferably, the walls 146–154 are equally spaced in a vertical direction.

Openings 156, 158, 160 and 162 in cylindrical side wall 144 are provided between walls 146 and 150, walls 150 and 152, walls 152 and 154, and walls 154 and 148 respectively.

Potential sensing electrodes 124 for each of the units 112–118 inclusive preferably take the form of a receptacle 164 joined to the underside of each of the intermediate walls 150–154 and bottom wall 146. The receptacles 154 are adapted to be filled with a suitable buffered electrolyte 132 whose ion value and ionic concentration are fixed.

Although not illustrated in FIG. 3 since the representation is in schematic form only, it is to be understood that at least a portion 128 of the bottom wall 146 and the intermediate walls 150–154 in alignment with the receptacles 164 making up sensing electrodes 124, are of special conductive glass presenting an ion activity sensing membrane equivalent to the membrane portion 28 of electrodes 24 of device 10.

The internal reference member 130 of the sensing electrode 124 of unit 112 is in contact with the buffered electrolyte 132 within receptacle 164 of unit 112. The electrode 124 extends outwardly of the receptacle 164 of the sensing electrode forming a part of unit 112 and is connected to one terminal of meter 140 by electrically conductive wire 138. The internal reference members 130 of the sensing electrodes 124 associated with units 114, 116 and 118 are also in contact with the buffered electrolyte 132 within respective receptacles 164. Reference elements 134 electrically connected to each of the internal reference members 130 extend downwardly into the units 112, 114, and 116 such that the reference elements will contact test solution in each of the units 112, 114 and 116. The reference element 134 associated with unit 118 and extending through top wall 148 is adapted to be electrically connected to the opposite terminal of potential measuring meter 140 by a line 142 which may also have a control switch therein similar to switch 44. The element 134 of unit 118 also extends downwardly into the interior thereof such that it will contact the test solution in that unit.

In the operation of device 110, it is understood that the medium to be tested for the ionic activity thereof is introduced into the interior of each of units 112–118 through respective openings 156–162 at least to a level such that the test solution 122 contacts a corresponding reference element 134. Measurement of the ionic activity as a function of the potential value again is conducted in normal fashion with the signal being amplified in the manner previously described. The solution may readily be removed from each of the compartments defined by units 112–118 inclusive by simply tilting the body to one side and allowing the solution to run out through openings 156–162. The interior of the individual compartments may readily be rinsed out using a conventional pipette or water bottle.

Figure 6:
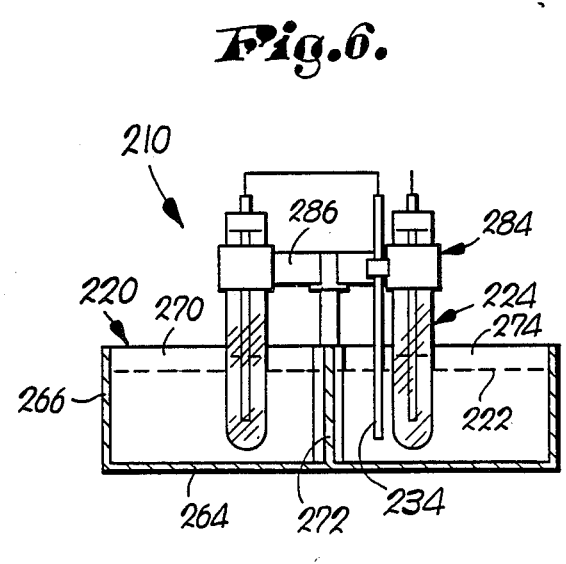
FIG. 6 is a vertical cross-sectional view through a forward part of the device shown in FIG. 5.
Figure 7:
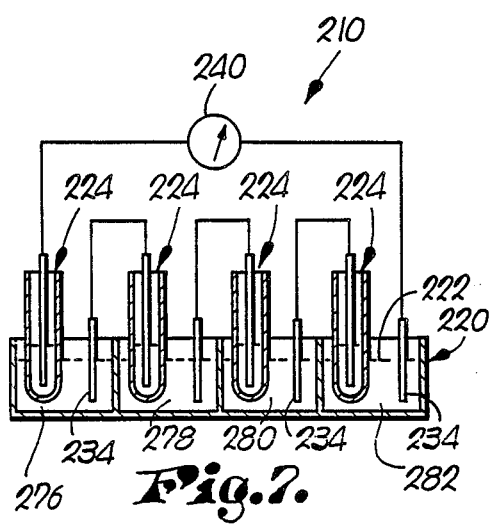
FIG. 7 is a vertical cross-sectional schematic representation of the device shown in FIG. 5.

The third embodiment of the invention as shown in FIGS. 5–7 comprises a device 210 which has an open topped cylindrical tray or vessel 220 made up of a circular bottom wall 264 and a circumscribing, upright side wall 266. Four radially extending interior walls 268, 270, 272 and 274 divide the vessel 220 into four separate compartments 276, 278, 280 and 282.

A central spider 284 carried by the zone of juncture of divider walls 268–274 inclusive has four radially extending legs 286 which are designed to overlie respective compartments 276–282 in bisecting relationship thereto.

Each of the legs 286 supports a potential sensing electrode 224 and a reference element 234 which are each similar to the electrodes 24 and elements 34 of device 10. It is to be noted from FIG. 6 that the electrodes 224 and elements 234 carried by each of the legs 286 of spider 284 are disposed such that they will be immersed in a test solution 222 received in each of the compartments 276–282 inclusive. The electrical arrangement of the device 210 is schematically illustrated in FIG. 7 wherein it can be seen that the electrodes 224 and elements 234 are all in electrical series relationship and connected to potential measuring meter 240 in a manner identical to the electrical connection of device 10 illustrated in FIGS. 1 and 2. The solution 222 received in compartments 276–282 inclusive must be of identical composition in order to provide an accurate reading on meter 240.

Although preferred embodiments of the invention have been illustrated, it is to be understood that the principles hereof may be accomplished using other specific devices which are capable of amplifying the voltage produced by individual potential sensing electrodes and reference elements. The principal requirement is that the electrodes and elements be connected in electrical series relationship and joined to the terminals of a single meter so that the potential signal response is amplified to increase the sensitivity of the reading. In this manner, a potential measuring meter may be employed in many instances that is not as sensitive as would otherwise be required for potential measurements at very low voltage levels.

I claim:

1. A multiple membrane electrode device for amplifying the signal potential directed to a potential measuring apparatus, said device comprising:
   a plurality of ion selective potential sensing electrodes each having a potential sensing membrane which is functional as a capacitor;
   means for receiving a quantity of liquid solution to be tested for the ionic concentration thereof, said receiving means including a plurality of separate solution receiving compartments, each isolating the solution received therein from electrical contact with solution received in the other solution receiving compartments, there being a separate solution receiving compartment for each of the sensing electrodes, each of the sensing electrodes being disposed with the membrane thereof in a position adapted to be in contact with a quantity of the test solution received in a corresponding solution receiving compartment;
   an electrically conductive element associated with each of the sensing electrodes, each element being disposed to be in electrical contacting relationship with the liquid test solution in a respective compartment;
   means for electrically coupling the sensing electrodes and the elements in electrical series relationship; and
   means for connecting one of the sensing electrodes and one of the elements to the potential measuring apparatus.

2. The invention of claim 1, wherein the endmost sensing electrode and the opposite electrically endmost element are adapted to be connected to said potential measuring apparatus.

3. The invention of claim 1, wherein each of the solution receiving compartments comprises a separate vessel adapted to contain a quantity of the solution to be tested for the ionic concentration thereof and of a size to accommodate a corresponding sensing electrode and a sufficient quantity of the solution to be tested such that the solution may contact the membrane of the corresponding potential sensing membrane.

4. The invention of claim 1, wherein said solution receiving compartments are constructed as a single vessel, each of said compartments being of a size to accommodate a corresponding sensing electrode and a sufficient quantity of the solution to be tested such that the solution may contact the membrane of the corresponding potential sensing membrane.

5. The invention of claim 4, wherein said vessel is essentially cylindrical in configuration, the compartments being radially disposed about the cylindrical configuration.

6. The invention of claim 1, wherein said solution receiving compartments are disposed in an integrally interconnected stacked arrangement.

7. The invention of claim 6, wherein the stacked arrangement defines a discrete body having a series of openings therein permitting introduction of a quantity of said solution and removal thereof from respective compartments.

8. The invention of claim 7, wherein each of the compartments is defined by a bottom wall and a circumscribing upright side wall, said sensing electrode being integrally joined to the bottom wall of a respective compartment with the membrane thereof forming a part of the bottom wall of an adjacent compartment.

9. The invention of claim 8, wherein each of the sensing electrodes has means disposed to electrically connect the corresponding sensing electrode with the solution to be tested for the ionic concentration thereof in the next adjacent compartment.

10. The invention of claim 1, wherein said solution receiving means comprises an elongated body having side wall structure and a top wall and a bottom wall at opposite ends thereof, there being a series of intermediate walls dividing the space between the top wall and bottom wall respectively to define said compartments, the side wall structure having an opening therein communicating with a corresponding compartment and located such that a quantity of the solution to be tested for the ionic concentration thereof may be introduced into a respective compartment and retained therein during the test thereon and to thereafter be removed from the corresponding compartment.

11. The invention of claim 10, wherein each of the sensing electrodes comprises a receptacle connected to the bottom wall below compartment thereabove and to each of the intermediate walls below a corresponding compartment thereabove, each of the intermediate walls and the bottom wall having a section defining the membrane of a corresponding sensing electrode and thereby positioned to contact test solution received in each of the compartments.

12. The invention of claim 11, further comprising electrically conductive means in each of the receptacles below an intermediate wall projecting into the compartment therebelow to an extent to contact solution to be tested in the compartment there next below.

13. The invention of claim 12, further comprising electrically conductive means projecting from the sensing electrode below the bottom wall and adapted to be connected to the potential measuring apparatus.

14. The invention of claim 13, further comprising electrically conductive means extending through the top wall for electrically connecting the test solution in the uppermost compartment to the potential measuring apparatus.

15. The invention of claim 10, wherein each of the sensing electrodes is adapted to contain a buffered electrolyte in contact with the membrane of a respective sensing electrode.

16. The invention of claim 15, further comprising electrically conductive means for connecting the electrolyte to the test solution in an adjacent compartment.

17. The invention of claim 1, wherein at least four sensing electrodes and four of said elements are provided in electrically series relationship.

18. The invention of claim 1, wherein said test solution receiving means comprises an open topped vessel having a series of side by side test solution receiving compartments separated by respective divider walls, there being spider means carried by the divider walls supporting the sensing electrodes and elements in each compartment respectively.

19. The invention of claim 1, wherein paired sensing electrodes and elements are each combined in a single unit.

20. A method of amplifying a potentiometrically measured ionic concentration signal comprising the steps of:
providing separate quantities of a liquid solution to be tested for the ionic concentration thereof, wherein each of said separate quantities of liquid solution are electrically isolated from one another;
measuring the potentiometric value of each of the separate electrically isolated test solutions; and
directing the current from each separate test solution in electrical series relationship to a potential measuring apparatus.

* * * * *